(12) United States Patent
Hilpert

(10) Patent No.: US 6,239,296 B1
(45) Date of Patent: May 29, 2001

(54) PROCESS FOR A PHENYLTHIOBUTYL-ISOQUINOLINE AND INTERMEDIATES THEREFOR

(75) Inventor: Hans Hilpert, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/513,148

(22) Filed: Feb. 25, 2000

Related U.S. Application Data

(62) Division of application No. 09/044,439, filed on Mar. 19, 1998, now Pat. No. 6,130,348.

(30) Foreign Application Priority Data

Apr. 10, 1997 (EP) .................................................. 97810212
Apr. 18, 1997 (EP) .................................................. 97810240

(51) Int. Cl.[7] ........................ C07D 303/04; C07C 321/02
(52) U.S. Cl. ................................................. 549/553; 560/9
(58) Field of Search ................................. 549/553; 560/9

(56) References Cited

U.S. PATENT DOCUMENTS

| 5,484,926 | 1/1996 | Dressman et al. | 546/114 |
| 5,705,647 | 1/1998 | Babu et al. | 546/146 |
| 6,018,066 | 1/2000 | Inaba et al. | 558/49 |

FOREIGN PATENT DOCUMENTS

WO 97/11938  4/1997  (WO).

OTHER PUBLICATIONS

Sasaki, et al. A Novel Approach to the Synthesis of Optically Pure Non–Protein $\alpha$–amino Acids In Both L & D Configuration from L–Serine, Tetrahedron Letters, vol. 28, No. 48, pp. 6069–6072 (1987).

*Primary Examiner*—Zinna Northington Davis
(74) *Attorney, Agent, or Firm*—George W. Johnston; William H. Epstein; F. Aaron Dubberley

(57) ABSTRACT

Intermediate compounds useful for making phenylthiobutyl-isoquinoline compounds of formula

II

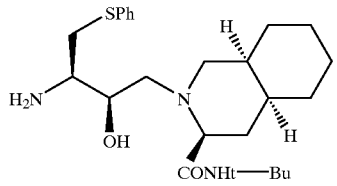

11 Claims, No Drawings

PROCESS FOR A PHENYLTHIOBUTYL-ISOQUINOLINE AND INTERMEDIATES THEREFOR

This is a divisional of application(s) Ser. No. 09/044,439 filed on Mar. 19, 1998 now U.S. Pat. No. 6,130,348.

BACKGROUND OF THE INVENTION

The compound phenylthiobutyl-isoquinoline of the formula

II and its preparation starting from L-serine is described, e.g., in U.S. Pat. No. 5,484,926, incorporated herein by reference. This compound is a valuable intermediate for the manufacture of pharmacologically active compounds, suitable for the treatment of viral infections, especially those caused by HIV and other retroviruses, described in U.S. Pat. No. 5,484,926, e.g., at columns 16 and 17, such as represented by formula

I wherein Ph is phenyl
and pharmaceutically acceptable salts thereof.

SUMMARY OF THE INVENTION

The present invention relates to a new method for making compounds of formula

II and intermediates for making compounds of formula II.

The compounds of this invention are useful intermediates for the manufacture of pharmacologically active compounds suitable for the treatment of viral infections, particularly, those caused by HIV and other retroviruses.

The method of the present invention is characterized by less reaction steps, more convenient reaction conditions and a higher overall yield of the desired stereoisomer of formula II. Particularly, in accordance with the method of the present invention, protection of a carbamate group of an intermediate phenylthio compound by a silyl group leads to a considerable increase in yield compared to that of prior methods for making compounds of formula II.

DETAILED DESCRIPTION OF THE INVENTION

The method of the present invention comprises (a) reacting diprotected L-serine of formula

VIII wherein R is lower alkyl and $R^1$ is lower alkyl or benzyl, with mesyl or tosyl chloride and a thiophenolate;

(b) reacting the resulting phenylthio compound of formula

VII with halogenated methyllithium;

(c) reducing a resulting halogen ketone of formula

VI wherein X is halogen, to the corresponding halogen alcohol of formula

V (d) treating the halogen alcohol of formula V with a base to form the [(R)-1-[(S)-oxiran-2-yl]-2-phenylthio-ethyl]carbamic acid ester of formula

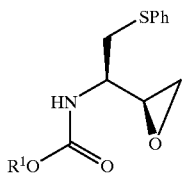

IV (e) reacting the carbamic acid ester of formula IV with N-tert.-butyl-decahydro-(4aS, 8aS)-isoquinoline-3(S)-carboxamide of formula

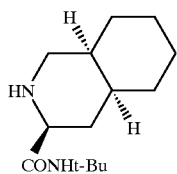

X and
(f) treating the resulting compound of formula

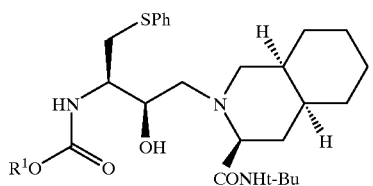

III with a base to yield the compound of formula II above.

The term "lower-alkyl" used throughout the specification and claims refers to straight- or branched-chain saturated hydrocarbon residues with 1–6, preferably 1–4, carbon atoms, such as methyl, ethyl, n-propyl, isopropyl, n-butyl, sec.-butyl, tert.-butyl, a pentyl or a hexyl group with methyl and ethyl being preferred, especially for $R^1$. Especially preferred in connection with the present invention are compounds wherein $R^1$ is methyl. Halogen denotes chlorine, bromine and iodine with chlorine being preferred.

The starting diprotected L-serines of formula VIII are known compounds and can easily be prepared from L-serine via reacting the corresponding L-serine lower alkyl esters with the corresponding chloroformates.

The phenylthio compounds of formula VII may be prepared using methods known in the art (e.g. Sasaki et al., Tetrahedron Letters 28, 6069 (1987)). The amino- and carboxy-protected L-serine is transformed into its tosylate or mesylate in the presence of an amine such as pyridine or triethylamine in an aprotic solvent such as methylene chloride or acetic acid ester and then reacted with a thiophenolate. The thiophenolate can be prepared in situ from thiophenol and a strong base, at low temperature, preferably a temperature from −10° C. up to 0° C.

Any conventional halomethylating agent can be used to halomethylate the phenylthio compounds of formula VII to form the halogen ketone compounds of formula VI. The halomethylation of the resulting phenylthio compound VII is preferably effected using halogenated methyllithium which is generated in situ. The latter is conveniently formed using dihalogenated methane, e.g., dichloro-, dibromo- or diiodomethane, preferably using bromochloromethane, and a lower-alkyl-lithium, such as, for example, butyllithium or hexyllithium, in an ether, preferably tetrahydrofuran, at −20° to −120° C., preferably −80° C.

In accordance with the method of the present invention, the halomethylation of the phenylthio compound VII to the halogen ketone VI is carried out by (a) silylating a carbamate group of a compound of formula VII in the presence of a lower-alkyl-lithium to form a silyl-protected compound; and (b) alkylating the silyl-protected compound in the presence of dihalogenated methane with a lower-alkyl-lithium to produce a halogen ketone of formula VI.

Preferred silyl-protected compounds of the present invention include compounds of the general formula VII-A and/or VII-B formed as an intermediate

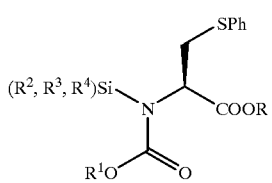

VII-A

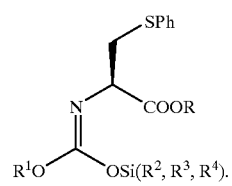

VII-B

In accordance with the present invention, any conventional method for producing the silyl-protected compounds of formulas VII-A and VII-B can be used. Suitable silylating agents for use with the present invention include organochlorosilanes of the formula $ClSi(R^2, R^3, R^4)$, wherein $R^2$, $R^3$ and $R^4$ are lower-alkyl or phenyl. A preferred organochlorosilane is chlorotrimethylsilane.

The method of the present invention for making the halogen ketone of formula VI provides new and unexpected results. Surprisingly, the protection of the carbamate group present in compound VII by a silyl group yielding compounds VII-A and/or VII-B as intermediates leads to a considerable increase in yield of the halogen ketone compounds of formula VI. Furthermore, this novel method for producing the halogen ketone compounds of formula VI can be used in a process for making the compounds of formula II to provide increased yields of the compounds of formula II compared to prior methods.

In accordance with the present invention, any conventional means can be used to alkylate the silyl-protected compounds of formula VII-A and VII-B. Preferred alkylating agents are lower-alkyl-lithium compounds such as butyllithium or hexyllithium. Moreover, an almost complete halomethylation of the phenylthio compounds of formula VII can be achieved using significantly less lower-alkyl-lithium and dihalogenated methane compared to amounts typically used in conventional halomethylation methods. In accordance with the present invention, the halogen ketone VI can be reduced to the corresponding alcohol of formula V with a hydride in a solvent such as toluene, tetrahydrofuran or an alcohol, preferably methanol, ethanol or isopropanol, at a temperature between −30 and 80° C., preferably between −15° C. and 50° C., optionally under reduced pressure, using sodium bis-(2-methoxy-ethoxy)-aluminium hydride, lithium aluminium hydride, lithium aluminium tri-tert.-butoxyhydride, sodium borohydride, tetramethylammonium borohydride or, preferably, using an aluminium tri-alkoxide or lithium aluminium tri-alkoxyhydride. The term "alkoxide" means lower alkoxy with the lower-alkyl residue being as defined above, such as, e.g., methoxy, ethoxy, n-propoxy, isopropoxy, n-butoxy, or isobutoxy, tert.-butoxy, as well as pentyloxy or hexyloxy groups. The aluminium compounds can have identical or different alkoxy groups. Aluminium tri-isopropoxide and aluminium tri-sec.-butoxide are especially preferred compounds. The reagents lithium aluminium tri-tert.-butoxyhydride, aluminium tri-isopropoxide and aluminium tri-sec.-butoxide gave unexpected high stereoselectivity in a molar ratio of at least 9:1 of the (1S,2S) and (1S, 2R) isomeric halohydrins V, which could be crystallized in >99% optical purity and with high yield.

The ring closure of the halohydrin of formula V to form the corresponding epoxide of formula IV can be carried out by conventional means, such as in a solvent, for example, ethanol or preferably, a toluene/water mixture in the presence of a base such as an alkaline or alkaline earth metal hydroxide, preferably sodium or potassium hydroxide, at a temperature between 0° and 80° C., preferably 40–50° C. The epoxide which is formed need not be purified.

The reaction of the epoxide of formula IV with the isoquinoline X to form compound III can be carried out by any conventional means, such as, in a solvent, for example, a hydrocarbon, such as toluene, or a lower-alkanol, preferably ethanol, while heating under reflux, at preferably 20–100° C., and most preferably 80° C.

The cleavage of the N-protecting group from the compound of formula III can be carried out by any conventional means such as, in a solvent, for example, water, ethanol or a mixture thereof, using a base such as sodium or potassium hydroxide while heating to the reflux temperature, preferably 20–100° C., especially 80° C.

A further aspect of the present invention is the new intermediate compounds of formulas VII, VI, V, IV and VIII wherein $R^1$ is lower alkyl, namely, compounds of formulas VII-1. VI-1, V-1, IV-1 and III-1, as well as the use of these new intermediate compounds for the preparation of the compound of formula II or pharmacologically active compounds suitable for treating viral infections, such as the compound of formula I and their salts mentioned above. A preferred embodiment of the new compounds of this invention are those wherein $R^1$ is $C_{1-3}$ alkyl, especially methyl or ethyl.

Especially preferred compounds of formulas III, IV, V, VI and VII are those wherein R and $R^1$ are methyl and X is chlorine, such as methyl (1R, 2R)-[1-phenylthiomethyl-3-[(3S, 4aS, 8aS)-3-tert.-butoxycarbamoyl-decahydroisoquinol-2-yl]-2-hydroxypropyl]-carbamate;

methyl [(R)-1-[(S)-oxiran-2-yl]-2-phenylthio-ethyl]-carbamate;

methyl (1R, 2S)-[3-chloro-2-hydroxy-1-(phenylthiomethyl)-propyl]-carbarnate;

methyl [3-chloro-2-oxo-(R)-1-(phenylthiomethyl)-propyl]-carbamate and methyl (3-phenylthio-(R)-2-methoxycarbonylamino)-propionate.

Finally, the compounds of formulas II, III, IV, V, VI and VII, when obtained by the method described hereinbefore or in the following Examples, are a further aspect of the present invention.

A compound of formula I can be obtained, e.g., in accordance with the method described in Example 23 of U.S. Pat. No. 5,484,926, using 70 mg of the compound of formula II, 24.6 mg of 3-hydroxy-2-methylbenzoic acid, 33 mg of DDC and 22mg of $HOBTH_2O$ in 4 ml of THF.

The formation of pharmaceutically acceptable salts can be performed by conventional methods known in the art. The methanesulfonic acid salt, e.g., can be prepared as described in Example 75 of U.S. Pat. No. 5,484,926 by dissolving 3.34 g of compound I in 30 ml of MeOH and 30 ml of methylene chloride and adding a solution of 596 mg of methanesulfonic acid in 10 ml of methylene chloride dropwise and working up of the reaction mixture to obtain the desired compound in pure form.

Reaction Scheme I summarizes the preferred reaction steps for the preparation of compounds VIII to I wherein R and $R^1$ are methyl and X is chlorine, This reaction scheme is described in more detail in the examples of the specification.

REACTION SCHEME I

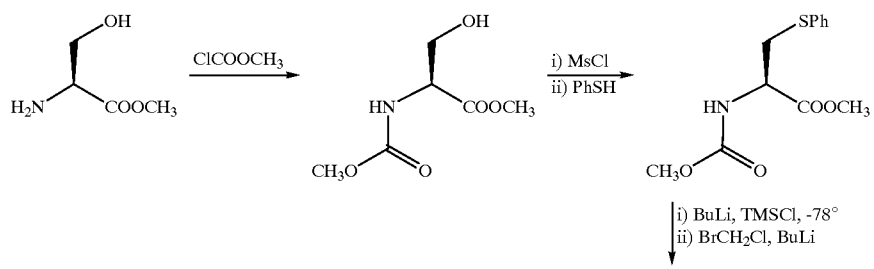

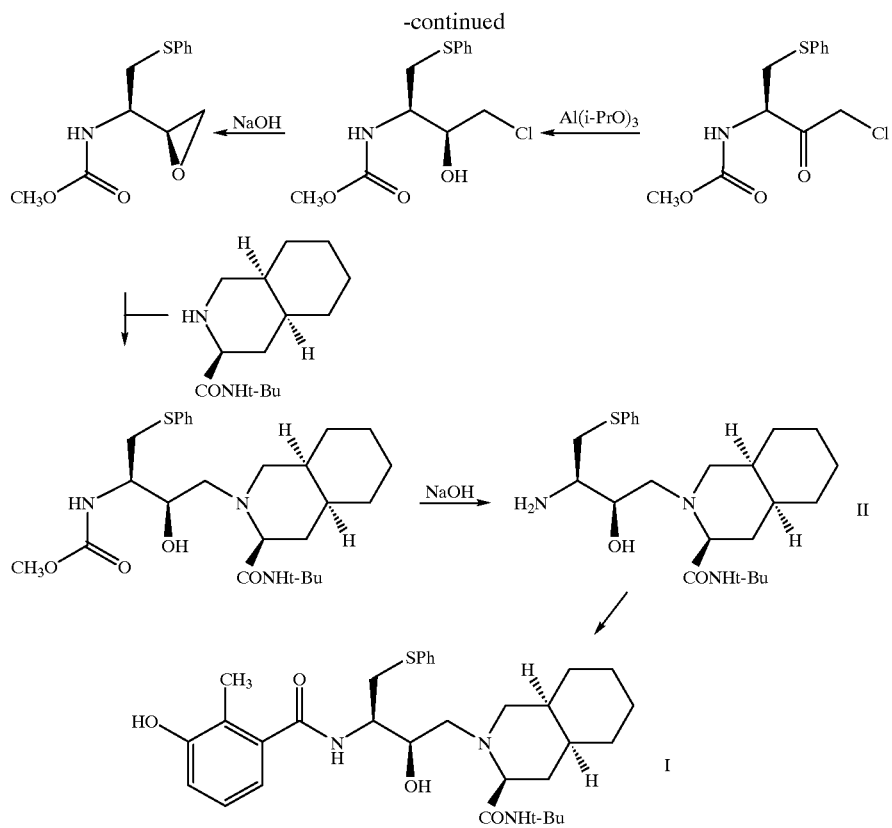

The following Examples illustrate the present invention in more detail without limiting it.

EXAMPLE 1

To a solution of 72.03 g L-serine-methylester hydrochloride in 400 ml of water were added at 0° C. 49.5 g of methyl chloroformate. The pH was kept at 6–7 by adding a 40% aqueous solution of sodium hydroxide. After 2½ h at 0° C. the mixture was extracted with 6 portions of ethyl acetate, the combined extracts were dried and evaporated to give 75.39 g (92%) of pure methyl 3-hydroxy-(S)-2-methoxycarbonylamino-propionate. IR (neat): 3380 m (NH, OH), 1720s, br. (C=O), 1535s (amide II). MS (EI): 178/20 (M+H$^+$).

EXAMPLE 2

To a solution of 8.86 g of methyl 3-hydroxy-(S)-2-methoxycarbonylamino-propionate and 5.73 g of methanesulfonyl chloride in 80 ml of ethyl acetate were added at −10° C. 5.06 g of triethylamine. After 1 hour at −10° C. the mixture was washed with diluted aqueous hydrochloric acid (1N) and water, the ethyl acetate was evaporated and the residue was dissolved in 15 ml of dimethylformamide. The solution was treated at −20° C. with a solution of 7.41 g of sodium thiophenolate in 30 ml of dimethylformamide and stirring was continued at −20° C. for 5 hours. The mixture was diluted with water and extracted with toluene and the toluene was evaporated to give 13.22 g (98%) of pure methyl (3-phenylthio-(R)-2-methoxycarbonylamino)-propionate. IR (neat): 3350w (NH), 1745s and 1702s (C=O), 1513s (amide II). MS (EI): 269/20(M$^+$).

EXAMPLE 3

To a solution of 8.08 g of methyl (3-phenylthio-(R)-2-methoxycarbonylamino)- propionate in 75ml of tetrahydrofuran were added at −80° C., 18 ml of a 1.67M solution of butyllithium in hexane followed by addition of 3.58 g of chlorotrimethylsilane. The suspension was treated with 4.66 g of bromochloromethane followed by addition of 27 ml of a 1.67M solution of butyllithium in hexane at −80° C. The solution was quenched with 50 ml of 6% aqueous hydrochloric acid and warmed to 22° C. The layers were separated, the organic layer was washed with brine, dried and evaporated to give 8.70 g approx. 70% pure methyl [3-chloro-2-oxo-(R)- 1-(phenylthiomethyl)-propyl]-carbamate. A sample was crystallized from tetrahydrofuran/hexane, m.p. 91–92.5° C. IR (KBr): 3321s (NH), 1740s and 1681s (C=O), 1539s (anide II). MS (EI): 287/15 (M$^+$).

EXAMPLE 4

To a suspension of 2.15 g aluminium isopropoxide in 35 ml of isopropanol were added 2.88 g of methyl [3-chloro-2-oxo-(R)-1-(phenylthiomethyl)-propyl]-carbamate and the suspension was stirred at 70° C./400 mbar for 4 hours. The mixture was cooled to 0° C., the pH was adjusted to 1 by adding hydrochloric acid and the isopropanol was evaporated. The suspension was filtered and the residue was recrystallized from toluene to give 2.18 g (75%) isomerically pure methyl (1R, $^2$S)-[$^3$-chloro-2-hydroxy-1-(phenylthiomethyl)-propyl]-carbamate, m.p. 113–114° C. IR (KBr): 3389m and 3327m (NH,.OH), 1695s (C=O), 1537s (amide II). MS (EI) : 289/35 (M$^+$).

EXAMPLE 5

A mixture of 2.90 g of methyl (1R, $^2$S)-[3chloro-2-hydroxy-1-(phenylthiomethyl)-propyl]-carbamate, 0.8 g sodium hydroxide, 20 ml toluene and 10 ml of water was stirred at 40° C. for 2 hours. The organic layer was washed with water and the solvent evaporated. The residue containing methyl [(R)-1-[(S)-oxiran-2-yl]-2-phenylthio-ethyl]-carbamate was mixed with 12 ml of ethanol and 2.38 g of decahydro-(4aS,.8aS)-isoquinoline-3(S)-N-tert.-butylcarboxamide and heated at reflux temperature for 5–10 hours. The solvent was evaporated and the residue partitioned between water and dichloromethane. The organic layer was evaporated to give 4.4 g (90%) of methyl (1R, 2R)-[1-phenylthiomethyl-3-[(3S, 4aS, 8aS)-3-tert.-butoxycarbamoyl-decahydro-isoquinol-2-yl]-2-hydroxypropyl]-carbamate. IR (KBr): 3410m and 3320m (NH, OH), 1715s and 1660s (C=O), 1550s (amide II).

EXAMPLE 6

A suspension of 4.92 g of methyl (1R, 2R)-[1-phenyl-thiomethyl-3-[(3S, 4aS, 8aS)-3-tert.-butoxycarbaroyl-decahydroisoquinol-2-yl]-2-hydroxy-propyl]-carbamate and 2.69 g of sodium hydroxide in 10 ml of ethanol and 10 ml of water was heated at reflux for 3–5 hours. The solvent was evaporated and the residue was partitioned between water and dichloromethane. The organic layer was washed with water, dried and evaporated to give 3.9 g (90%) 2-[3(R)-amino-2(R)-hydroxy4-phenylthio-butyl]-decahydro-(4aS, 8aS)-isoquinoline-3(S)-N-tert.-butylcarboxamide.

EXAMPLE 7

To a solution of 240 g1 L-serine-methylester hydrochloride in 130 ml of water were added at 0° C. 29.8 g of benzyl chloroformate. The pH was kept at 6–7 by adding a 40% aqueous solution of sodium hydroxide. After 3 h at 0° C. the mixture was extracted with 5 portions of ethyl acetate, the combined extracts were dried and evaporated to give 37.12 g (95%) of pure methyl 3-hydroxy-(S)-2-benzyloxycarbonylamino-propionate. IR (neat): 3380m (NH, OH), 1720s, br. (C=O), 1540s (amide II).

EXAMPLE 8

To a solution of 8.86 g of methyl 3-hydroxy-(S)-2-benzyloxycarbonylamino-propionate and 4.00 g of methanesulfonyl chloride in 60 ml of ethyl acetate were added at −10° C. 3.54 g of triethylamine. After 1 hour at −10° C. the mixture was washed with diluted aqueous hydrochloric acid (1N) and water, the ethylacetate was evaporated and the residue was triturated with hexane. The crude mesylate was dissolved in 11 ml of dimethylformamide and treated at −20° C. with a solution of 5.19 g sodium thiophenolate in 22 ml of dimethylformamide. After 5 hours at −20° C. the mixture was diluted with water and extracted with toluene. The toluene was evaporated and the residue was crystallized from toluene/hexane (1:9, v/v) to give 9.5 g (79%) of pure methyl (3-phenylthio-(R)-2-benzyloxycarbonylamino)-propionate. IR (KBr): 3339m (NH), 1742s and 1681s (C=O), 1533s (amide II).

EXAMPLE 9

To a solution of 10.36 g of methyl (3-phenylthio-(R)-2-benzyloxycarbonylamino)-propionate in 80 ml of tetrahydrofuran were added at −80° C. 18 ml of a 1.67M solution of butyllithium in hexane followed by addition of 3.58 g of chlorotrimethylsilane. The suspension was treated with 4.66 g of bromochloromethane followed by addition of 27 ml of a 1.67M solution of butyllithium in hexane at −80° C. The solution was quenched with 55 ml of 6% aqueous hydrochloric acid and warmed to 22° C. The layers were separated, the organic layer was washed with brine, dried and evaporated to give 10.5 g approx. 75% pure benzyl [-3-chloro-2-oxo-(R)-1-(phenylthiomethyl)-propyl]-carbamate. IR (KBr): 3350s (NH), 1730s and 1685s (C=O), 1520s (amide II).

EXAMPLE 10

To a suspension of 2.15 g aluminium isopropoxide in 35 ml of isopropanol were added 3.64 g of benzyl [3-chloro-2-oxo-(R)-1-(phenylthiomethyl)-propyl]-carbamate and the mixture was stirred at 50° C./400 mbar for 4 hours. The mixture was cooled to 0° C., the pH was adjusted to 1 by adding hydrochloric acid and the isopropanol was evaporated. The residue was partitioned between water and dichloromethane and the organic layer was evaporated. The residue was chromatographed on silica to give 2.9 g (80%) of pure benzyl (1R, 2S)-[3-chloro-2-hydroxy-1-(phenylthiomethyl)-propyl]-carbamate. IR (KBr): 3360br (NH, OH), 1690s (C=O), 1540s (amide II).

What is claimed is:

1. A compound of formula

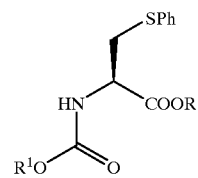

VII-1 wherein R is lower alkyl and $R^1$ is methyl or ethyl.

2. The compound of claim 1 wherein said compound is methyl (3-phenylthio-(R)-2-methoxycarbonylamino)-propionate.

3. A compound of formula

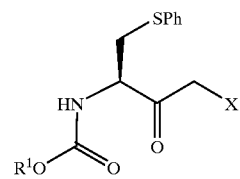

VI-1 wherein $R^1$ is lower alkyl and X is halogen.

4. The compound of claim 3 wherein $R^1$ is methyl or ethyl.

5. The compound of claim 3 wherein said compound is methyl [3-chloro-2-oxo-(R)-1-(phenylthiomethyl)-propyl]-carbamate.

6. A compound of formula

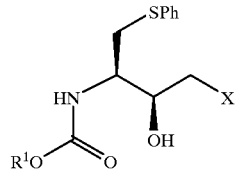

V-1 wherein $R^1$ is lower alkyl and X is halogen.

7. The compound of claim 6 wherein $R^1$ is methyl or ethyl.

8. The compound of claim 6 wherein said compound is methyl (1R, 2S)-[3-chloro-2-hydroxy-1-(phenylthiomethyl)-propyl]-carbamate.

9. A compound of formula

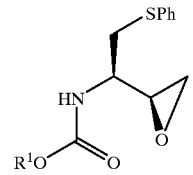

IV-1 wherein $R^1$ is lower alky.

10. The compound of claim 9 wherein $R^1$ is methyl or ethyl.

11. The compound of claim 9 wherein said compound is methyl [(R)-1-[(S)-oxiran-2-yl]-2-phenylthio-ethyl]-carbamate.

* * * * *